US008824630B2

(12) United States Patent
Maurer, Jr. et al.

(10) Patent No.: US 8,824,630 B2
(45) Date of Patent: Sep. 2, 2014

(54) METHOD AND APPARATUS FOR TREATING A TARGET'S PARTIAL MOTION RANGE

(75) Inventors: Calvin R. Maurer, Jr., Mountain View, CA (US); Jay B. West, Mountain View, CA (US)

(73) Assignee: Accuray Incorporated, Sunnyvale, CA (US)

( * ) Notice: Subject to any disclaimer, the term of this patent is extended or adjusted under 35 U.S.C. 154(b) by 373 days.

(21) Appl. No.: 13/281,354

(22) Filed: Oct. 25, 2011

(65) Prior Publication Data
US 2012/0106704 A1 May 3, 2012

Related U.S. Application Data

(60) Provisional application No. 61/408,511, filed on Oct. 29, 2010.

(51) Int. Cl.
A61B 6/03 (2006.01)
A61B 6/00 (2006.01)
A61N 5/10 (2006.01)
G21K 5/10 (2006.01)

(52) U.S. Cl.
USPC ........ 378/65; 378/8; 378/20; 378/68; 378/69; 378/95

(58) Field of Classification Search
USPC ........... 378/4–20, 65, 68, 69, 91, 95, 96, 114, 378/117, 145, 162, 204, 205, 207–210, 378/901; 600/407, 425–429
See application file for complete search history.

(56) References Cited

U.S. PATENT DOCUMENTS

| 5,398,684 | A |  | 3/1995 | Hardy |  |
|---|---|---|---|---|---|
| 6,326,963 | B1 |  | 12/2001 | Meehan |  |
| 6,496,598 | B1 |  | 12/2002 | Harman |  |
| 6,867,773 | B2 |  | 3/2005 | Hux |  |
| 7,227,925 | B1 |  | 6/2007 | Mansfield et al. |  |
| 7,551,717 | B2 | * | 6/2009 | Tome et al. | 378/65 |
| 7,609,810 | B2 | * | 10/2009 | Yi et al. | 378/65 |
| 2002/0049375 | A1 |  | 4/2002 | Strommer et al. |  |
| 2004/0015073 | A1 |  | 1/2004 | Schell et al. |  |
| 2005/0059887 | A1 |  | 3/2005 | Mostafavi et al. |  |
| 2005/0096515 | A1 |  | 5/2005 | Geng |  |
| 2005/0180544 | A1 |  | 8/2005 | Sauer et al. |  |

(Continued)

OTHER PUBLICATIONS

Tang et al., Fiducial Registration from a Single X-Ray Image: A New Technique for Fluoroscopic Guidance and Radiotherapy, S.L.Delp, A.M. DiGiogia, and B. Jaramaz (Eds.): MICCA/2000, LNCS 1935, 2000, pp. 502-511.

(Continued)

Primary Examiner — Anastasia Midkiff
(74) Attorney, Agent, or Firm — Lowenstein Sandler LLP

(57) ABSTRACT

A computing system determines a full motion range of a target, wherein the full motion range of the target defines an internal target volume (ITV). The computing system identifies a partial motion range of the target, wherein the partial motion range is a subset of the full motion range of the target. The computing system generates a partial-ITV based on the identified partial motion range, wherein the partial-ITV is a volume swept by the target as the target moves through the partial motion range, the partial-ITV being smaller than the ITV. The computing system generates a treatment plan to deliver treatment to the partial-ITV.

22 Claims, 12 Drawing Sheets

(56) References Cited

U.S. PATENT DOCUMENTS

| | | | |
|---|---|---|---|
| 2006/0036170 | A1 | 2/2006 | Lachaine et al. |
| 2006/0050847 | A1 | 3/2006 | Jaffray et al. |
| 2006/0100509 | A1 | 5/2006 | Wright et al. |
| 2006/0291621 | A1 | 12/2006 | Yan et al. |
| 2007/0071176 | A1* | 3/2007 | Main et al. .................. 378/207 |
| 2007/0127845 | A1 | 6/2007 | Fu |
| 2007/0274577 | A1 | 11/2007 | De Font-Reaulx-Rojas |
| 2008/0130825 | A1 | 6/2008 | Fu et al. |
| 2008/0177279 | A1 | 7/2008 | Sumanaweera et al. |
| 2008/0298540 | A1 | 12/2008 | Serban et al. |
| 2009/0052623 | A1 | 2/2009 | Tome et al. |
| 2009/0110145 | A1 | 4/2009 | Lu et al. |
| 2009/0180678 | A1 | 7/2009 | Kuduvalli et al. |
| 2011/0107270 | A1 | 5/2011 | Wang et al. |
| 2011/0166407 | A1 | 7/2011 | Sumanaweera et al. |

OTHER PUBLICATIONS

Rhode et al., Registration and Tracking to Integrate X-Ray and MR Images in an XMR Facility, IEEE Transactions on Medical Imaging, Nov. 2003, pp. 1369-1378, vol. 22, No. 11.

Supplementary European Search Report for European Patent Application No. 08870643.7, dated Dec. 30, 2010, 14 pages.

Dongshan Fu, et al., "Xsight Lung Tracking System: A Fiducial-Less Method for Respiratory Motion Tracking:," Jan. 1, 2007, Treating Tumors That Move with Respiration, Springer, DE, pp. 264-282, XP009142170, ISBN: 978-3-540-69885-2.

Yelin Suh et al., "Geometric uncertainty of 2D projection imaging in monitoring 3D tumor motion:," Physics in Medicine and Biology, Taylor and Francis Ltd. London, GB, vol. 52, No. 12, Jun. 21, 2007, pp. 3439-34554, XP020112919, ISSN: 0031-9155.

Khamene A. et al., "Automatic registration of portal images and volumetric CT for patient positioning in radiation therapy:," Medical Image Analysis, Oxford University Press, Oxford, GB, vol. 10, No. 1, Feb. 1, 2006, pp. 96-112, XPO25154071, ISSN: 1361-8415.

Zhiping Mu et al., "Multiple Fiducial Identification Using the Hidden Markov Model in Image Guided Radiosurgery:," Computer Vision and Pattern Recognition Workshop, 2006 Conference on New York, NY, USA, Jun. 17-22, 2006, Piscataway NJ, USA, IEEE, Piscataway, NJ, USA, Jun. 17, 2006, pp. 92-92, XP010922904.

BrainLAB: "IGRT ExacTrac® Brochure", Oct. 15, 2007, XP002613785, URL: http://web.archive.org/web/20071015153601/www.brainlab.com/downloaded/pdf/IGTExacTracBrochure.pdf (retrieved on Dec. 10, 2010).

Communication dated Jan. 18, 2011 for European Patent Application No. 08870643.7, 1 page.

Ross I. Berbeco, Steve B. Jiang, Gregory C. Sharp, George T. Y. Chen, Hassan Mostafavi, Hiroki Shirato, "Integrated radiotherapy imaging system (IRIS): design considerations of tumour tracking with linac gantry-mounted diagnostic x-ray systems with flat-panel detectors", Institute of Physics Publishing, Physics in Medicine and Biology, PH: S0031-9155 (04)68365-5, Phys. Med. Biol. 49 (2004) pp. 243-255.

PCT International Search Report and Written Opinion of the International Searching Authority mailed Mar. 20, 2009, for serial No. PCT/US08/13644 filed Dec. 11, 2008.

USPTO Office Action dated Jul. 25, 2011 for U.S. Appl. No. 12/199,293.

USPTO Notice of Allowance dated Aug. 25, 2011 for U.S. Appl. No. 12/199,293.

Brown, W.T. et al. (2009). "Application of Robotic Stereotactic Radiotherapy to Peripheral State I Non-small Cell Lung Cancer with Curative Intent," Clinical Oncology 21:623-631.

Schweikard, A. et al. (2005). "Respiration Tracking in Radiosurgery without Fiducials," Int. J. Medical Robotics and Computer Assisted Surgery 1(2):19-27.

Kilby, W. et al. (Oct. 2010). "The CyberKnife Robotic Radiosurgery System in 2010," Technology in Cancer Research and Treatment 9(5):433-452.

International Search Report and Written Opinion mailed Apr. 17, 2012, for PCT Patent Application No. PCT/US2011/058424, filed Oct. 28, 2011, 10 pages.

Rohlfing, T. et al. (Nov. 2005). "Markerless Real-Time 3-D Target Region Tracking by Motion Backprojection from Projection Images," IEEE Transactions on Medical Imaging 24(11):1455-1468.

* cited by examiner

METHOD AND APPARATUS FOR TREATING A TARGET'S PARTIAL MOTION RANGE

RELATED CASES

This patent application claims the benefit under 35 U.S.C. §119(e) of U.S. Provisional Application No. 61/408,511, filed Oct. 29, 2010, which is herein incorporated herein by reference in its entirety for all purposes.

TECHNICAL FIELD

Embodiments of the present invention relate to the field of image guided treatment and, in particular, to a system for identifying a target's motion range and treating a portion of that motion range.

BACKGROUND

A treatment target may move during image guided treatment such as radiation treatment. To account for such movement, traditional gantry-based radiation delivery systems treat the Internal Target Volume (ITV), i.e., the entire range of motion of the target during respiration or other movement, with a margin of expansion to compensate for setup inaccuracy, gross patient movement during treatment, and change of breathing pattern or other motion pattern between planning and treatment. This approach, however, comes with the drawback of large volumes of normal tissue being exposed to the prescription dose, especially in cases where the tumor undergoes a large excursion during breathing.

BRIEF DESCRIPTION OF THE DRAWINGS

The present invention is illustrated by way of example, and not by way of limitation, in the figures of the accompanying drawings.

DETAILED DESCRIPTION

Figure 1:
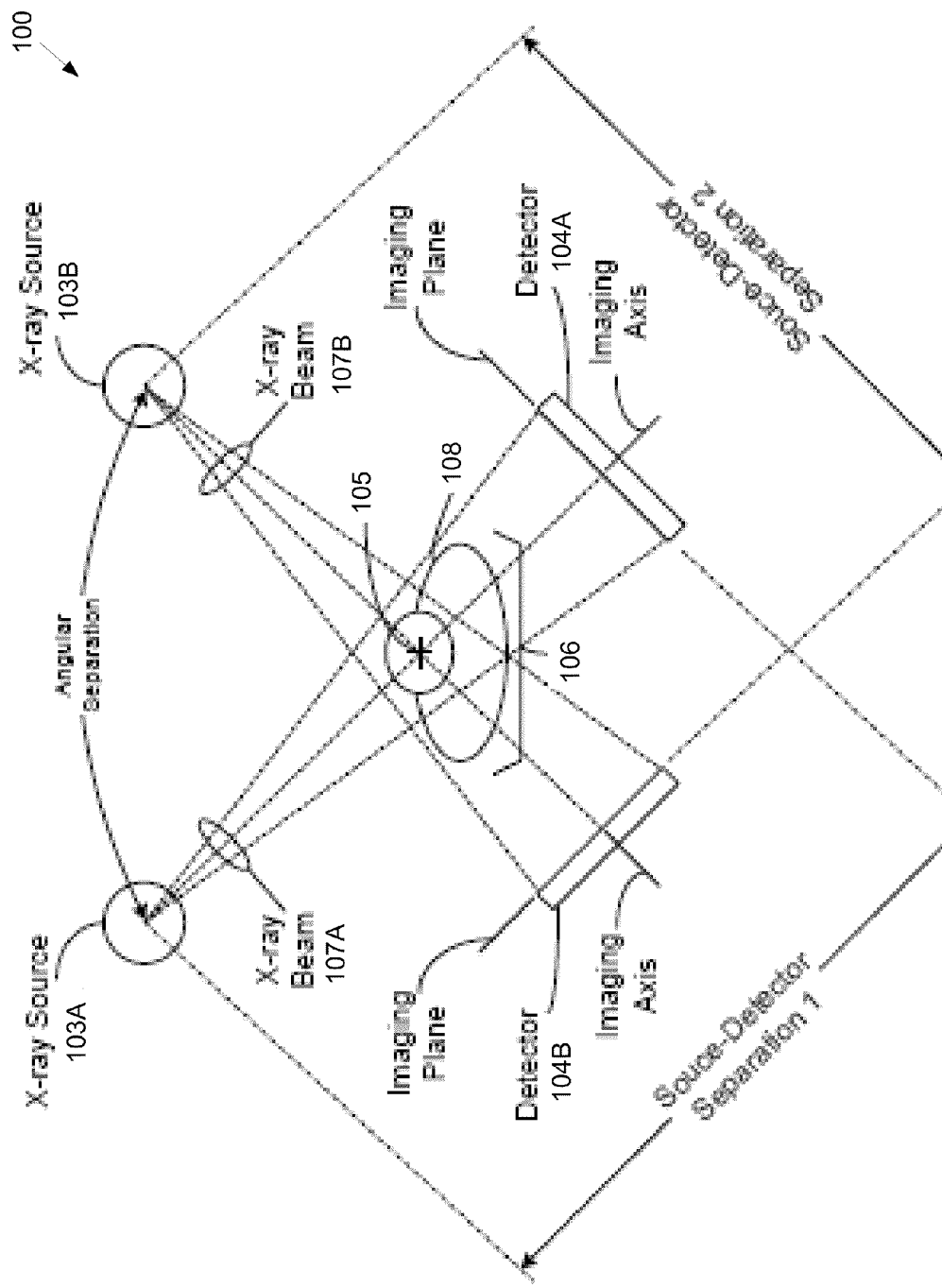
FIG. 1 illustrates a diagnostic imaging system, which may be a component of a treatment delivery system.

Described herein is a method and apparatus for treating a partial motion range of a target. In one embodiment, the method or apparatus determines a full motion range for the target and generates an internal target volume (ITV) that is the volume defined by the target as it moves through its full range of motion. The ITV may be considered to be the union of all volume occupied by the target during a motion cycle (e.g., a respiratory and/or cardiac cycle). The method or apparatus then identifies a partial motion range, which may not be tracked, the partial motion range being a subset of the full motion range. The method or apparatus then generates a partial-ITV that is the volume covered by the target as the target moves through the partial motion range. Treatment may then be delivered to a location covered by the partial-ITV.

One type of treatment in which the partial-ITV may be used is radiation treatment. Radiation treatment includes both radiation surgery (radiosurgery) and radiation therapy (radiotherapy). Radiotherapy and radiosurgery differ in the amount of radiation delivered to a patient in a treatment session. The amount of radiation in an individual session or fraction utilized in radiotherapy treatment sessions is typically about an order of magnitude smaller, as compared to the amount used in a radiosurgery session. For convenience, the term "radiation treatment" is used herein to mean radiosurgery and/or radiotherapy unless otherwise noted by the magnitude of the radiation.

Some pathological anatomies (e.g., tumors and lesions) may change position during treatment. For example, tumors in the human body may move with respiration and/or heartbeat. In radiosurgery, accurate knowledge of trajectories of the radiation beams through the patient anatomy to the lesion or tumor being treated can be critical in order to achieve the radiation dose distribution that was computed during treatment planning time. For treatment targets that move, for example due to breathing or heartbeat, it is important to take such motions into consideration during treatment planning and delivery.

Systems can account for target motion, as described above, by irradiating or treating the entire volume defined by the motion of the target (referred to as a no-view tracking mode). Alternatively, the target location may be precisely tracked during treatment using one or more tracking modes, and the system can deliver treatment by repositioning the treatment beam to follow the target motion, such as with the CyberKnife® Radiosurgery System by Accuray® Incorporated. Examples of tracking modes that may be used to track a target location include a 1-view tracking mode and a 2-view tracking mode. In some situations, the system cannot detect or compensate for motion in all directions. In such circumstances, a partial-ITV may be defined by the motion range of the target in the direction or directions that cannot be tracked. The partial-ITV, by virtue of being defined by only a portion of the target's full motion range, is smaller than an ITV, and therefore less healthy tissue receives unwanted treatment than with conventional systems that treat the entire ITV.

A system can account for target motion using various treatment modes in addition to using various tracking modes. In one embodiment, the system uses a gated treatment mode. In the gated treatment mode, the system times delivery of radiation treatment beams to correlate to specific phases of a patient's respiration cycle (or other motion cycle). In a standard treatment mode, no gating is used.

FIGS. 1-4E illustrate a 1-view tracking method (1-view tracking mode) that may be used to treat a tumor, in accordance with embodiments of the present invention. The 1-view tracking mode tracks a target (e.g., a tumor) in a single imaging plane. The 1-view tracking method may use a combination of real time tracking and a fixed offset from a patient's spine (or other reference structure) to allow for tracking a tumor that is only viewable in a single imaging plane. While 1-view tracking is used, all motion that occurs within the single imaging plane can be tracked and compensated for. Motion in the axis of the image (e.g., motion normal to the imaging plane) however cannot be tracked. Accordingly, position and motion may be divided into two parts: in-plane position and motion (which refers to the components of these quantities in the stack of planes normal to a source-detector axis that is used to acquire the images) and out-of-plane position and motion (which refers to the corresponding components along the source-detector axis). For 1-view tracking, a partial ITV may be generated that accounts for the out-of-plane motion range.

FIG. 1 illustrates a diagnostic imaging system 100, which may be a component of a treatment delivery system. In the diagnostic imaging system 100, x-ray sources 103A and 103B are separated by an angular separation for stereoscopic imaging of a volume of interest (VOI) in a patient 108 on a treatment couch 106. The x-ray sources 103A and 103B project x-ray beams 107A and 107B, respectively, through the patient 108 onto respective imaging detectors 104A and 104B. Each detector is characterized by an imaging plane and an imaging axis. The point where the imaging axes intersect defines the imaging isocenter 105 (also referred to herein as the treatment center).

Referring to FIG. 1, the x-ray detectors 104A and 104B periodically capture two-dimensional (2D) projection images of the VOI in the patient 108. Under optimal conditions, the system can 'see' the target VOI in both of the 2D projection images to provide stereoscopic imaging data. Alternatively, a single x-ray detector (e.g., detector 104A or 104B) may be used to capture non-stereoscopic imaging data. The system, as is known by the skilled artisan, may use the stereo imaging data in both views to determine and/or track precisely the target VOI location. For some patients, the system can only see the target VOI in one detector or image. In such situations, the system, in accordance with embodiments of the present invention, uses a 1-view tracking mode to track the target VOI's position during treatment. This situation may occur, for example, when the target VOI is superimposed on other x-ray attenuating structures such as the heart or spine in a particular view. Alternatively, a single view may be used even if the target VOI is visible in both views (e.g., if there is a higher correlation confidence in one of the views or if a user selects a specific view to be used). For the purposes of this discussion, it will be assumed that a tumor is only visible in images taken by detector 104B (or that images taken by detector 104B have a higher correlation confidence), and thus that a 1-view tracking mode based on images taken by detector 104B (referred to herein as 1-view B tracking mode) will be used for target tracking.

Figure 2A:
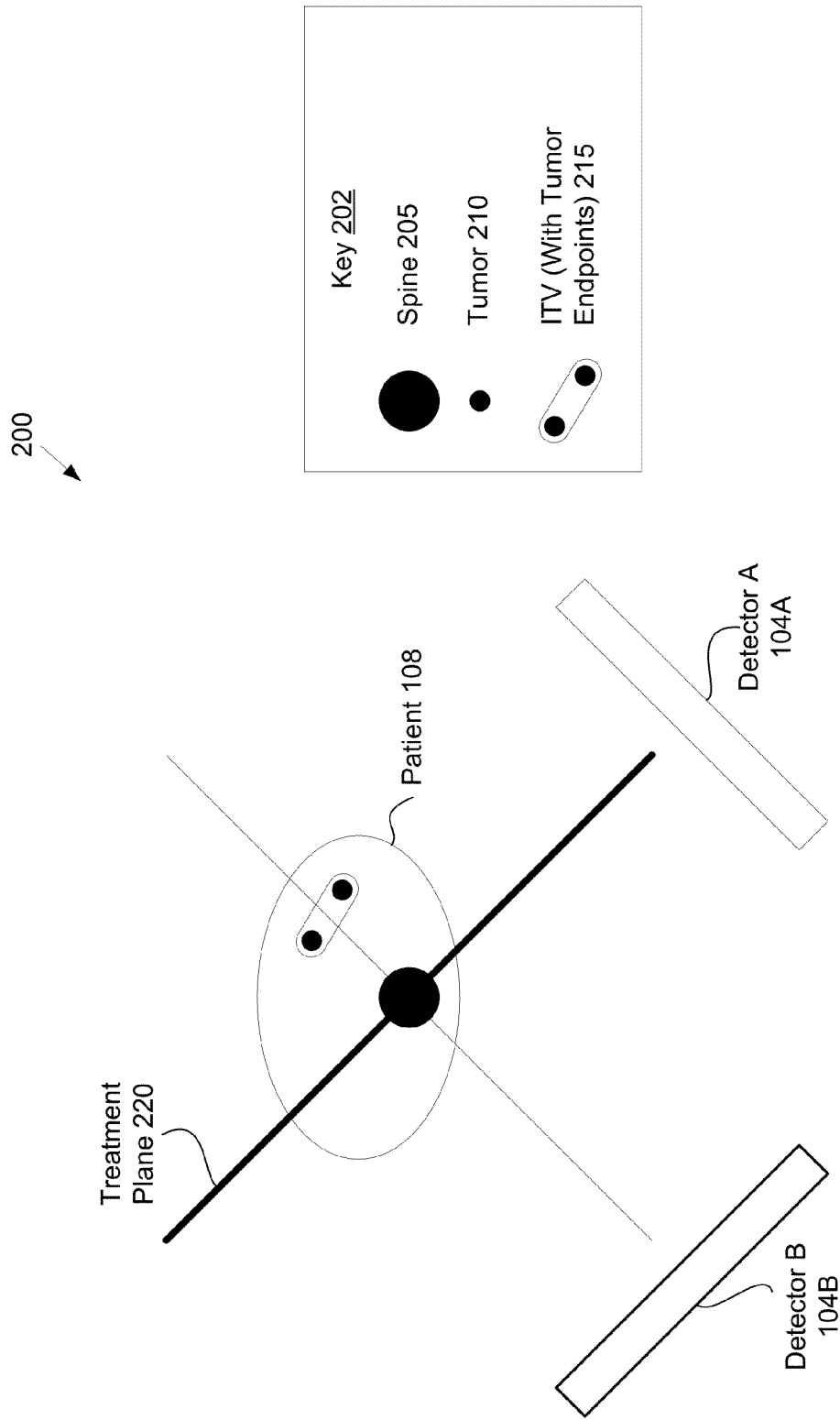
FIG. 2A illustrates a simplified view of the imaging system of FIG. 1, including internal anatomical structures within a patient.

FIG. 2A illustrates a simplified view 200 of the imaging system 100 of FIG. 1, including internal anatomical structures within the patient 108. FIG. 2A includes a key 202 that identifies a spine 205, a tumor 210 and an internal target volume (ITV) 215. An internal target volume is the volume defined by the target as it moves through its full range of motion. As shown in this embodiment, the patient's spine 205 is first aligned to the treatment center (i.e., the intersection of the imaging axes). This may be performed by positioning the treatment couch 106 that holds the patient 108. The system sees the spine 205 in both detectors 104A and 104B. Accordingly, the system aligns the spine 205 in three dimensional space by registering current stereoscopic x-ray images taken by the detectors 104A, 104B to DRRs generated from a preoperative CT scan, as will be appreciated by the skilled artisan.

A treatment plane 220 is shown intersecting the spine 205. The treatment plane 220 is a plane that is parallel to the imaging plane of the detector used for tracking (e.g., detector 104B) and that passes through the treatment center. When tracking a target using the 1-view tracking mode, the system determines, from the 1-view available, target VOI locations in the two dimensions of the imaging plane of the detector used for tracking (e.g., detector 104B). The 2D position data may be projected onto the treatment plane to provide a three dimensional coordinate position from the 2D position data.

Figure 2B:
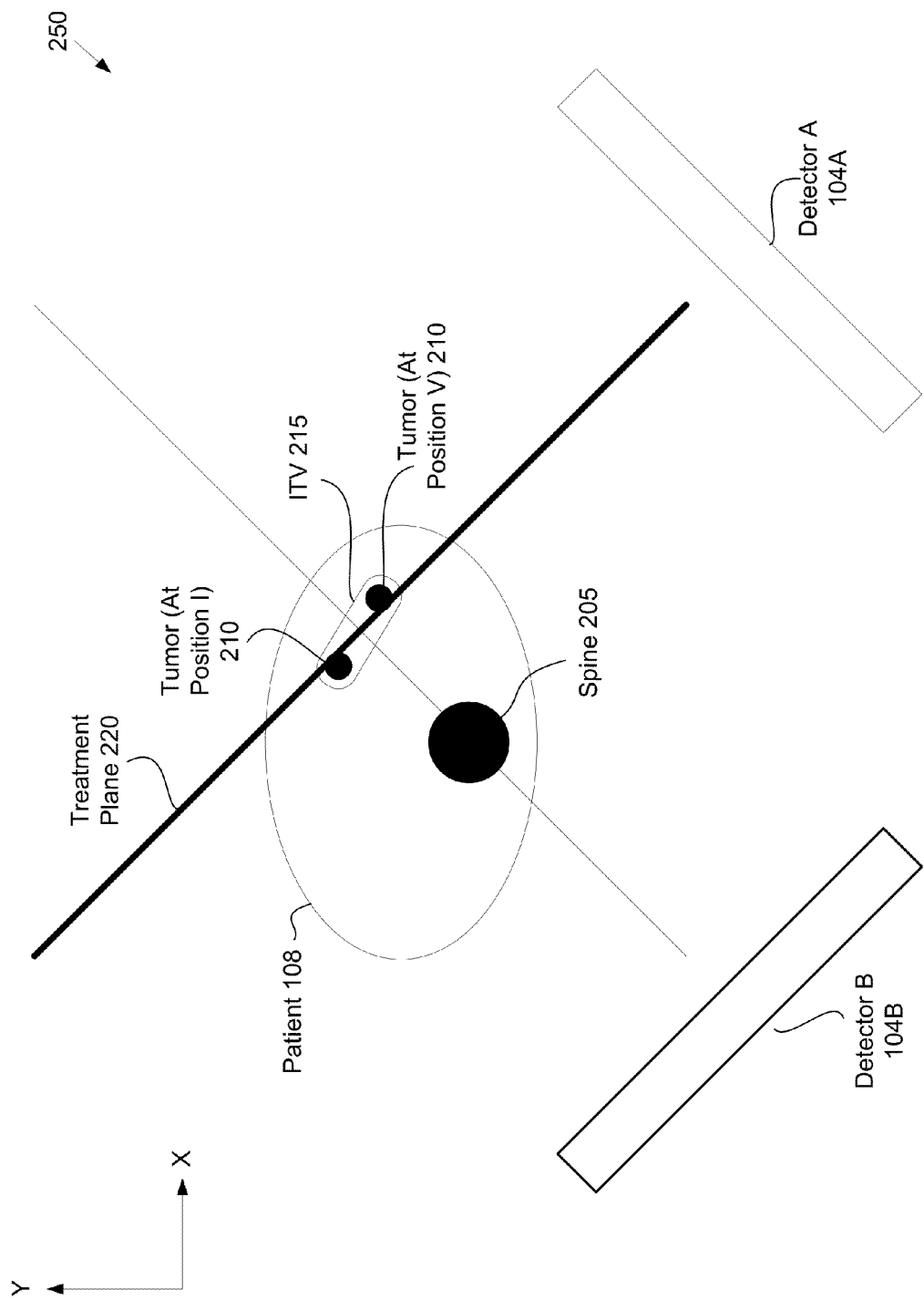
FIG. 2B illustrates a simplified view of the imaging system of FIG. 1, after a treatment couch has been repositioned so that a treatment center passes through the center of an ITV (Internal Target Volume).

In one embodiment, once the system aligns the spine (or other reference structure) to the treatment center, the system repositions a treatment couch that holds the patient so that the treatment center passes through the center of the ITV 215. Nominally, the treatment couch 106 is moved based on a predetermined offset between the spine 205 and a center of the ITV 215, as provided by a treatment plan. FIG. 2B illustrates a simplified view 250 of the imaging system 100 of FIG. 1, after the treatment couch 106 has been repositioned so that the treatment center passes through the center of the ITV 215, and before treatment is begun.

After the treatment couch 106 is moved based on the predetermined offset, a user (e.g., a physician or technician) may adjust a position of the treatment couch 106 to make alignment corrections. In one embodiment, after the initial offset motion, the position of the treatment couch 106 is tightly controlled. In one embodiment, alignment motions out of the treatment plane 220 are not allowed. For example, FIG. 2B shows an x-axis and a y-axis. A user would not be permitted to make an adjustment along just the y-axis or just the x-axis, because this would cause motion outside of the treatment plane 220. Thus, any adjustment in the x-axis would need to be accompanied by a corresponding adjustment in the y-axis. Similarly, any adjustment in the y-axis would need to be accompanied by a corresponding adjustment in the x-axis. This ensures that the offset between the spine 206 and the center of the ITV 215 in the axis perpendicular to the treatment plane 220 is not changed.

Figure 3A:
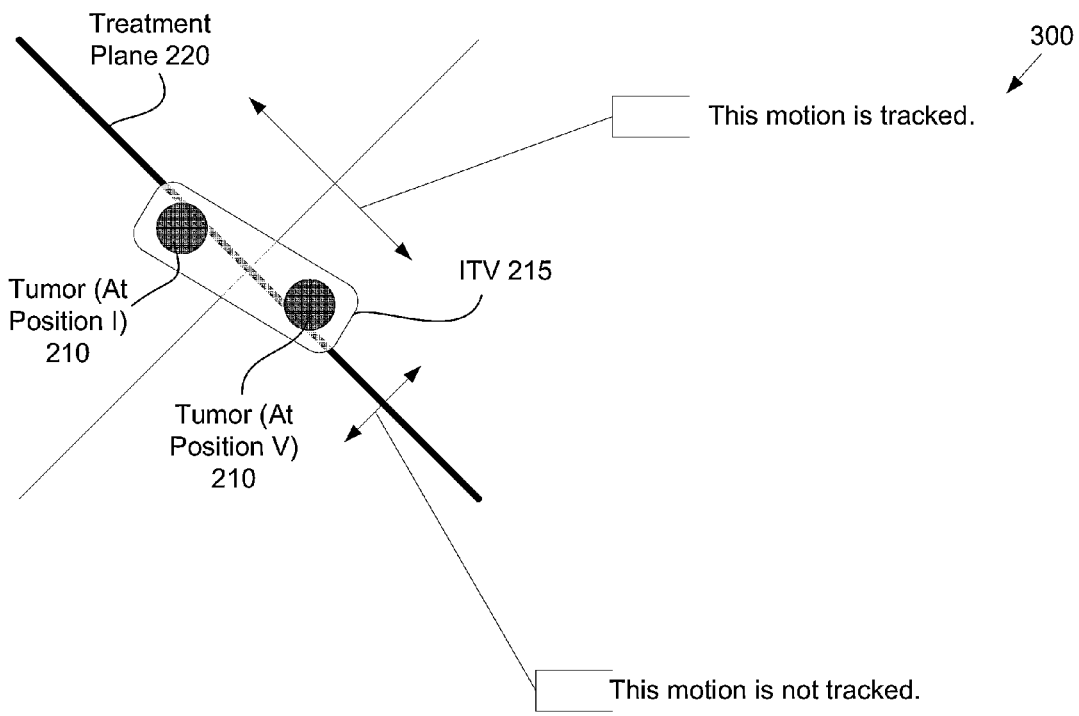
FIG. 3A shows a zoomed in view of an ITV, showing that motion within a treatment plane is tracked, while motion normal to the treatment plane is not tracked.
Figure 3B:
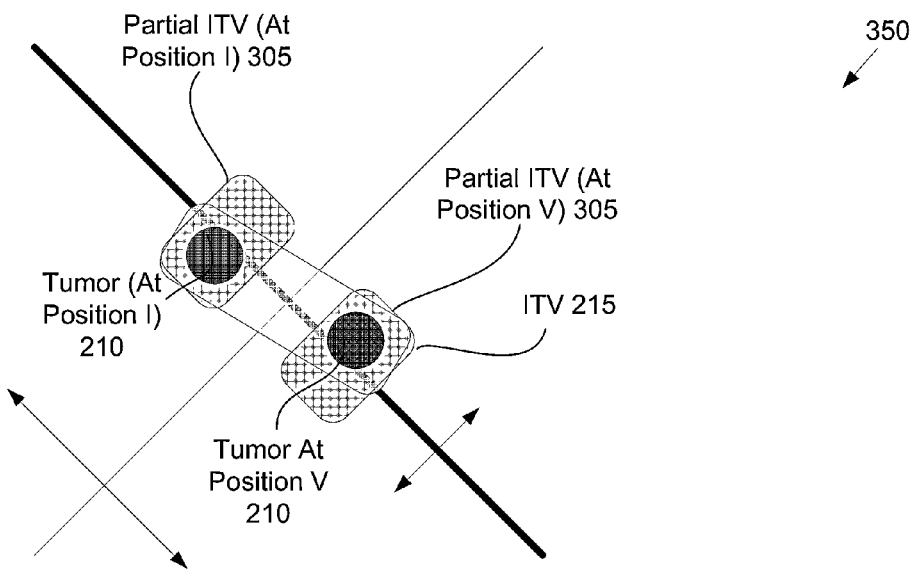
FIG. 3B shows another zoomed in view of the ITV, showing a partial-ITV that has been generated by projecting the motion onto the axis normal to the treatment plane.
Figure 4A:
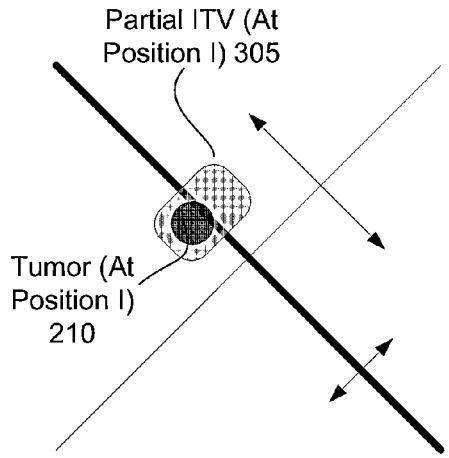
FIGS. 4A-4E show different positions of the tumor during a patient's respiratory cycle.
Figure 4B:
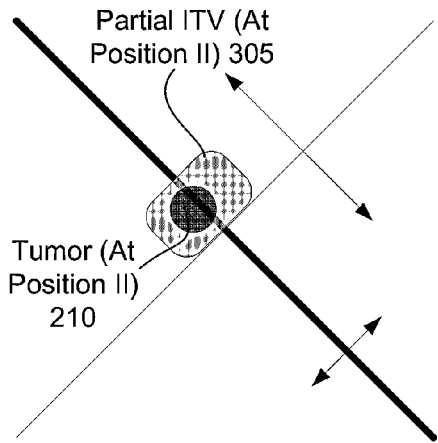
Figure 4C:
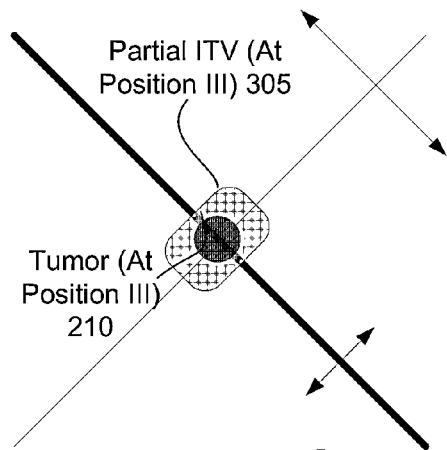
Figure 4D:
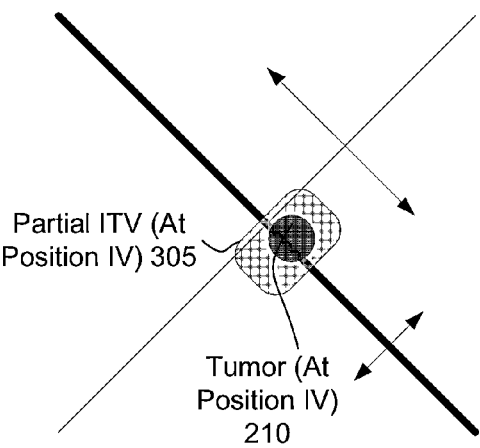
Figure 4E:
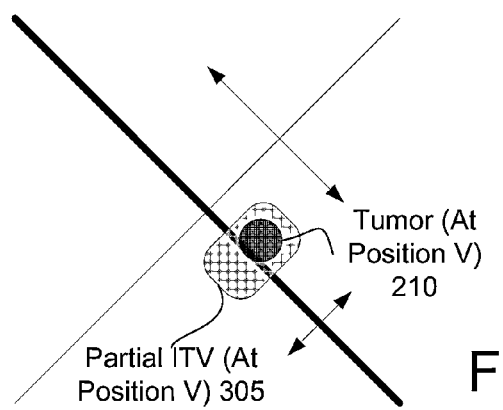

FIG. 3A shows a zoomed in view 300 of the ITV 215, in accordance with one embodiment of the present invention, showing that motion within the treatment plane 220 is tracked, while motion normal to the treatment plane 220 is not tracked. FIG. 3B shows another zoomed in view 350 of the ITV 215, showing a partial-ITV 305. In one embodiment, the partial-ITV 305 is generated by projecting the ITV 215 onto the axis normal to the treatment plane 220. This may be performed, for example, by representing the ITV as a three dimensional vector and projecting the three dimensional vector onto the axis normal to the treatment plane. This provides the component of the tumor's 210 motion along the axis normal to the treatment plane 220. The tumor 210 and partial ITV 305 are shown at a first position (position I) and at a fifth position (position V). As shown, the partial-ITV 305 is moved inside the treatment plane 220 as the tumor's 210 position changes. However, the partial-ITV 305 is not moved along the axis that is normal to the treatment plane 220.

FIGS. 4A-4E show different positions (e.g., positions I-V) of the tumor 210 during a patient's respiratory cycle. Tumor movement within the treatment plane 220 can be tracked using detector 104B. However, movement outside of or normal to the treatment plane cannot be tracked because the other detector cannot see the tumor. The system accounts for target VOI motion outside of the treatment plane 220 by treating the partial-ITV 305, and the system tracks and accounts for motion within the treatment plane.

In one embodiment, the system uses a radiation treatment beam to generate diagnostic images. In this embodiment, the system includes a device called an electronic portal imaging device (EPID). The EPID is positioned so as to receive radiation beams generated by a radiation treatment source that have passed through a patient. An EPID uses the radiation treatment beam itself to create portal images that can be used to determine a location of the target VOI. In one embodiment, the EPID includes a two-dimensional area detector, and thus can detect target VOI position within an imaging plane. For such EPIDs, the above described 1-view tracking mode can be used to track target VOI location. For example, the system may generate a partial-ITV by projecting an ITV onto the axis that is normal to the EPIDs imaging plane, as described above.

In one embodiment, the EPID includes a one-dimensional scanning detector. The one-dimensional scanning detector detects target VOI position within an imaging axis. When using an EPID that includes a one-dimensional scanning detector, the system may generate a partial-ITV by projecting the ITV onto the plane to which the imaging axis is normal. Thus, the partial-ITV may account for target VOI motion outside of the imaging axis.

In one embodiment, the system performs a technique called gating (also referred to herein as a gated treatment mode). In the gated treatment mode, the treatment beam is enabled when the estimated target location is within a predefined range, and disabled when the estimated target position is outside this range. The estimation of the target position may take place by direct measurement (for example, by localizing the target in one or more X-ray images), or may take place by a surrogate measurement (for example, by tracking optical markers attached to the exterior of the patient's chest). For a gated treatment mode, the motion range covered by the partial-ITV may span those positions for which the treatment beam will be turned on. For example, the treatment beam may be activated while the tumor is estimated to be within 5 mm of a full exhale tumor position. The partial-ITV may include the motion range of the tumor within those 5 mm. Gating may be used to accommodate cyclic patient motion such as respiratory motion or cardiac motion. In one embodiment, gating is combined with 1-view tracking or with tracking using an EPID. In such an embodiment, the partial-ITV may cover motion of the target VOI in an untracked plane or axis that occurs within a predetermined treatment zone (e.g., during a particular phase of the patient's respiratory cycle). The advantage of using a partial-ITV in conjunction with a gating system, and using the allowed motion range of the gating system to define the partial-ITV, is that the dose distribution displayed at the treatment planning step accurately reflects the amount of tissue that will be exposed to radiation during treatment delivery.

Figure 5:
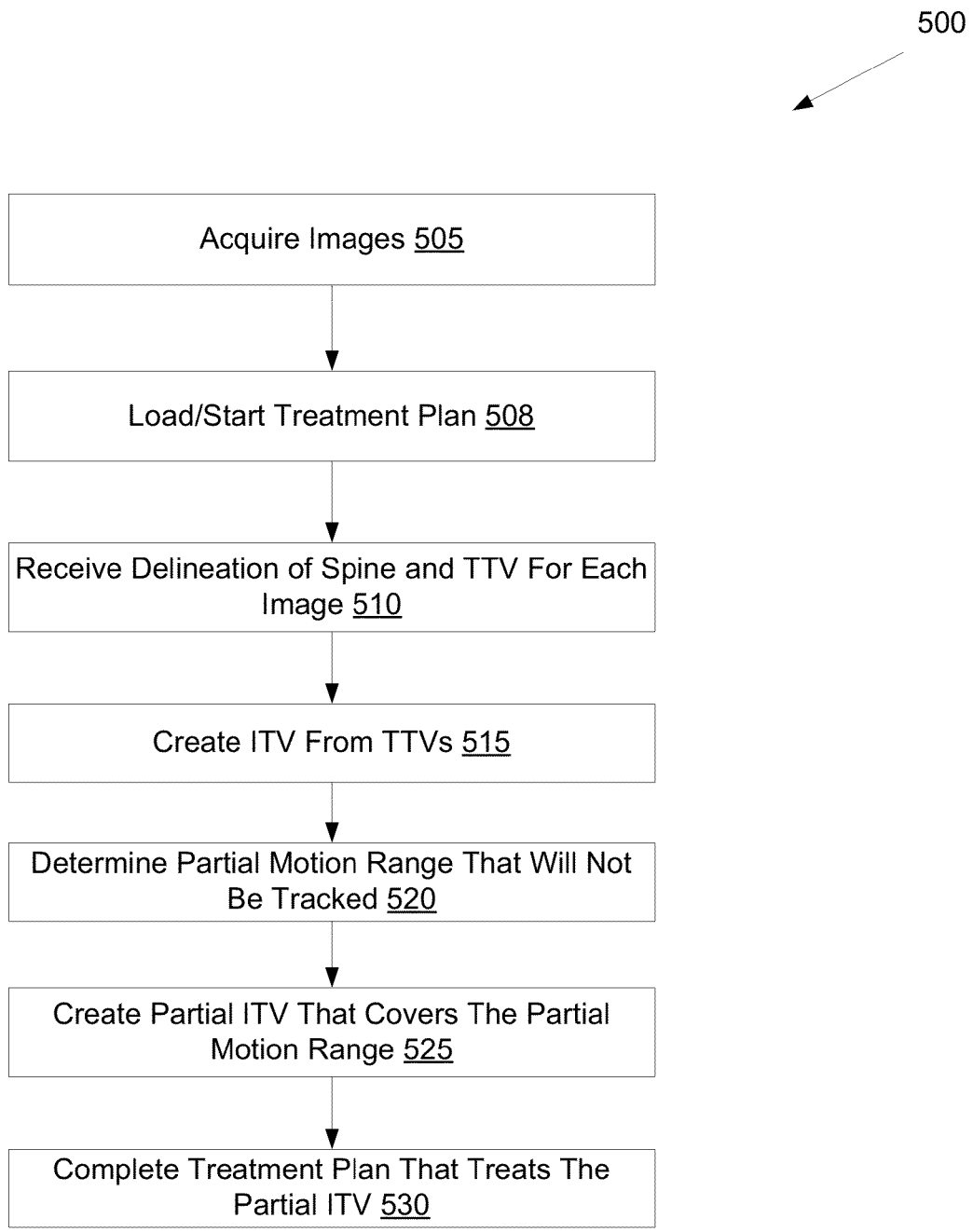
FIG. 5 illustrates a flow diagram for a method of treating a partial motion range of a pathological anatomy.

FIG. 5 illustrates a flow diagram for a method 500 of treating a partial motion range of a pathological anatomy. In one embodiment, method 500 is performed by one or more systems, such as an image acquisition system, a treatment planning system and/or a treatment delivery system. The actions of some blocks may be described as being performed by a particular system for convenience. However, it should be understood that these actions may alternatively be performed by systems other than those specifically described herein.

In block 505 of method 500, one or more images are acquired. In one embodiment, the images are computed tomography (CT) scan images. Alternatively, the images may be magnetic resonance imaging (MRI) scans or positron emission tomography (PET) scans. For the purposes of this discussion, the images will be described as CT images.

In one embodiment, at least two 3D CT images of the anatomy to be treated are acquired by an image acquisition system. Two CT images may be acquired at each of the motion extremes of the anatomy. For example, a first CT image may be acquired while the patient holds his or her breath in an exhale position, and a second CT image may be acquired while the patient holds his or her breath in a full inhale position. This provides high quality images as well as a full range of motion to be expected of the tumor during respiration. Alternatively, a single CT image may be acquired, for example if the tumor will move only slightly throughout the respiratory cycle.

In another embodiment, a 4D CT study is acquired. A 4D CT study, as is well understood by the skilled artisan, is a CT scan taken over a period of time that records all of the positions of a moving volume over that extended period. The 4D CT study may define the entire motion range of the tumor, including the effects of hysteresis. However, it should be noted that the ability of the 4D CT study to give a complete view of motion during respiration should be balanced against the lower image quality typically provided by a 4D CT study as compared to a 3D CT image. In one embodiment, a 4D CT study is acquired along with a 3D CT image (e.g., a CT image taken while the user holds his breath in a full inhale or exhale position).

After image acquisition, a physician creates a treatment plan (or an existing treatment plan is loaded) using a treatment planning system, such as MultiPlan® made by Accuray Incorporated. A user may be asked to designate one of the imported CT images as a primary CT for the treatment plan. The planning system may also receive a selection of a treatment template and load the treatment template. A treatment template provides one or more pre-defined treatment planning parameters and settings applicable to the anatomical treatment region of interest. For example, a lung tumor template may include instructions for generating a model of a respiration cycle.

At block 508, a treatment plan is started or loaded. At block 510, a user is prompted to delineate volumes of interest (VOIs) such as target volumes and reference structures that may be used in tracking. The treatment planning system provides tools for a user to delineate these volumes. In one embodiment, the treatment planning system receives a delineation of a spine or other reference structure (e.g., another skeletal structure) and a tracking target volume (TTV) for each imported CT image. The TTV may be a representation of the visible mass in the CT image of the tumor that will be treated during treatment delivery.

At block 515, the treatment planning system creates an internal target volume (ITV) from the TTVs. The ITV is a 3D volume defined by the full 3D motion range of the TTV (covering every position for the tumor along all three axes). In one embodiment, the ITV may be further expanded into a PTV (Planning Target Volume) including a margin expansion to compensate for setup inaccuracy, gross patient movement during treatment, and change of breathing pattern between planning and treatment. The ITV and/or PTV may be treated in the case of a tracking method that tracks tumor position based on a position of a reference structure such as the spine or other skeletal structure (referred to herein as 0-view tracking since no images of the tumor itself are being used to track the tumor's location). The 0-view tracking method, however, comes with the drawback of exposing a large volume of normal tissue to the prescription dose, especially in cases where the tumor undergoes a large excursion during breathing. In another embodiment, the ITV and/or PTV is treated, and the ITV is aligned with the treatment beam by means of a cone-beam CT or 4D CT taken in the treatment room before radiation delivery begins.

At block 520, the treatment planning system determines a partial motion range that is a subset of the target's full motion range that will not or cannot be tracked. The target motion subset may correspond to target motion along an untracked axis, target motion within an untracked plane, and/or 3D target motion that occurs outside of a tracked range. In one embodiment, a user selects the partial motion range (e.g., using the tools provided to perform VOI delineation). In another embodiment, the user selects a tracking method, which causes a preset partial motion range to be selected. For example, if the user elects to track the target motion along a single imaging axis or imaging plane, then the partial motion range may be automatically selected for an untracked plane or axis, respectively.

At block 525, the treatment planning system creates a partial-ITV defined by the target's motion over the selected partial motion range. The size, shape and position of the partial-ITV may be determined based on a treatment technique to be used during treatment and/or a type of tracking method that will be used during treatment.

In one embodiment, a gated radiation treatment technique is used to treat the tumor. In such a gated radiation treatment technique, a respiration cycle is monitored during treatment delivery. When the patient is in a particular phase (or phases) of the respiration cycle, a radiation treatment beam may be activated, and when the patient is in other phases of the respiration cycle, the treatment beam is deactivated. For a gated treatment technique, the partial motion range covered by the partial-ITV may span those positions for which the treatment beam will be turned on. For example, the treatment beam may be activated while the respiratory phase is within 20% of the full exhale tumor position. The partial-ITV may include the motion range of the tumor within 5 mm, where 5 mm was determined at treatment planning time, for example by means of a 4D CT, to be the respiratory excursion expected in the 20% of the respiratory phase for which the beam will be activated In another embodiment, another type of gated radiation treatment technique is used to treat the tumor. In this type of gated radiation technique, the position of the target is monitored either directly (e.g., by direct visualization of the target in an X-ray image, by direct visualization in the X-ray image of one or more metal markers implanted in or near the target, or by a signal, such as a radiofrequency signal, emitted by one or more markers implanted in the target) or indirectly (e.g., by means of a correlation model allowing an external signal, such as position of the chest wall, to allow the target position to be predicted). The treatment beam may be deactivated when the target moves out of a predetermined range, and hence the partial-ITV will span only those positions where the beam will be activated.

In one embodiment, a tracking method that tracks target motion along a single axis is performed during treatment. This axis may be, for example, the axis aligned with the treatment beam. In such an embodiment, location of the tumor in the plane normal to the tracked axis is indeterminate. Accordingly, the partial-ITV is generated by projecting the motion onto a plane normal to the tracked axis, and creating the partial-ITV using the shape of the target and the projected motion. The partial-ITV covers the motion range of the tumor in the untracked plane.

In one embodiment, as described above, 1-view tracking is performed during treatment. For 1-view tracking, the tracked imaging plane may correspond to the imaging plane of an x-ray imager that received X-rays that passed through the neighborhood of the target during treatment. In such an embodiment, location of the tumor in the axis normal to the tracked plane is indeterminate. Accordingly, the partial-ITV is a projected ITV that is generated by projecting the motion onto the axis that is normal to the tracked imaging plane. The partial-ITV covers the motion range of the tumor in the untracked axis. A 1-view tracking method may be used, for example, when a tumor is only trackable in one imaging plane (e.g., if the tumor is occluded by another anatomical structure in the other imaging plane, or if only one X-ray detector is present). When a 1-view tracking method is used, target locations are found in 2D. The 2D tracking may be converted to 3D by projecting the 2D position onto a plane that is plane-parallel to a plane that intersects a treatment center. This plane is referred to as the treatment plane. In one embodiment, this plane is determined based on offset information that identifies an offset between the spine (or other reference structure) and a centroid of the ITV. In another embodiment, an image such as a cone-beam CT or 4D CT is taken in the treatment room prior to treatment delivery, and the position of the ITV in this image is used to align the treatment plane with the radiation beams.

At block 530, the treatment plan is completed. Completing the treatment plan may include generating a respiration model that determines the expected respiratory motion of internal reference structures and/or the tumor. In one embodiment, this respiration model will later be updated prior to treatment delivery and/or during treatment delivery. Alternatively, the respiration model may not be updated. Completing the treatment plan may also include determining an offset between a reference structure (e.g., the spine) and the centroid of the partial-ITV and/or of the ITV. Completing the treatment plan may also include determining one or more positions from which to deliver treatment beams, and an amount of radiation to deliver from each position.

A radiation treatment plan is a plan for the delivery of radiation treatment beams to the pathological anatomy of the patient from a number of directions, with one or more beams (having one or more shapes, angles or orientations, energies, etc.) being applied in each direction. The radiation treatment plan may include a selected tracking method, which may call for acquisition of a number and/or timing of intra-treatment diagnostic x-ray images, which are used to track the location of the target; diagnostic x-ray images being one example of intra-treatment data collected to track the position of the target. For example, and without limitation, diagnostic x-ray images are registered (as known by the skilled artisan) with pre-treatment or intra-treatment 3D image data. Moreover, the tracking method may include an imaging protocol that identifies, for example, an imaging modality to use (e.g., single x-ray projections, multiple x-ray projections, etc), an imaging algorithm or algorithms to use, whether to track fiducials or patient anatomy, etc. The term "x-ray image" as used herein may mean a visible x-ray image (e.g., displayed on a video screen) or a digital representation of an x-ray image (e.g., a file corresponding to the pixel output of an x-ray detector).

Figure 6:
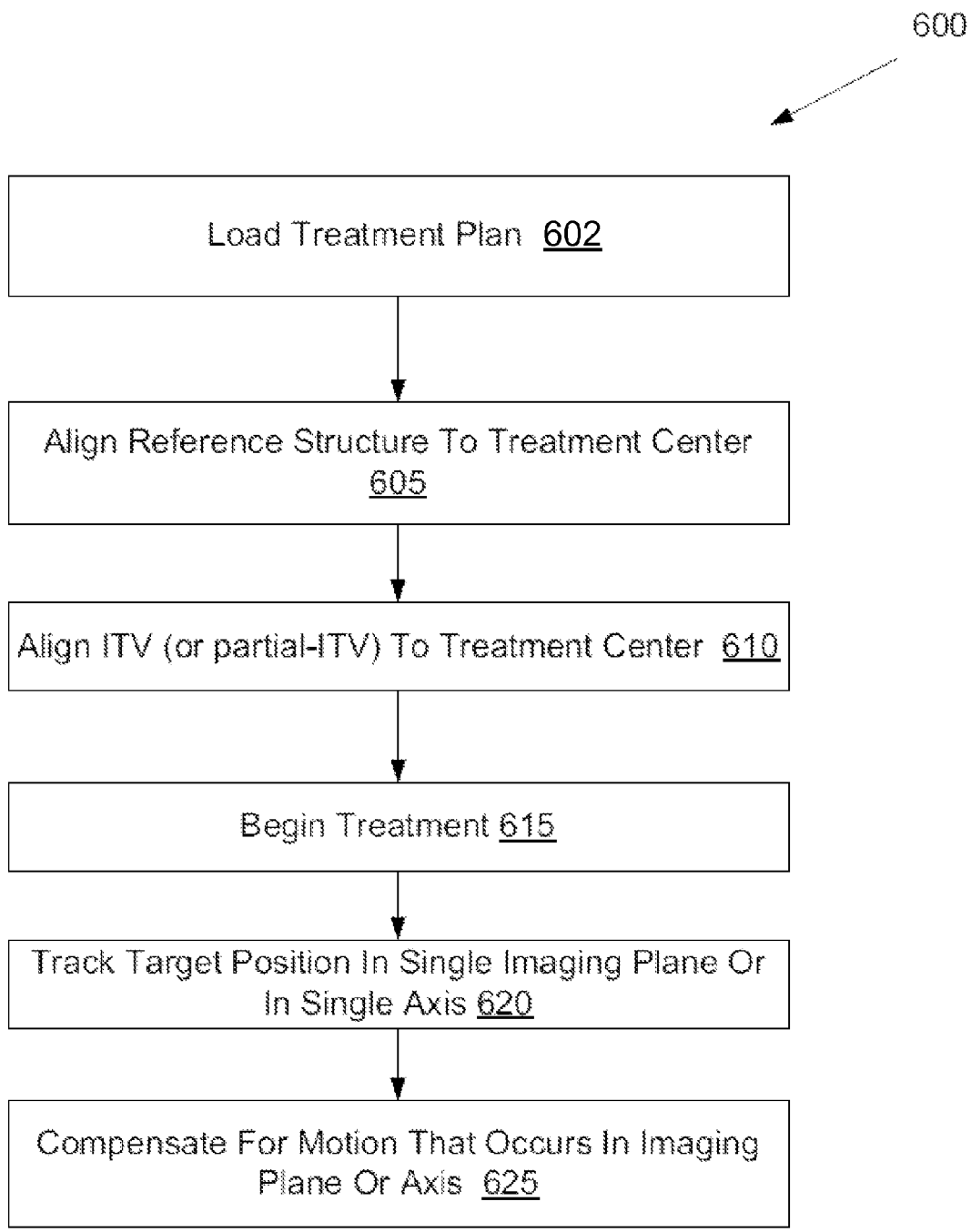
FIG. 6 illustrates a method of performing radiation treatment by a treatment delivery system that tracks target position in at least one axis, in accordance with one embodiment of the present invention.

FIG. 6 illustrates a method 600 of performing radiation treatment by a treatment delivery system that tracks target position in at least one axis, in accordance with one embodiment of the present invention. At block 602 of method 600, the treatment delivery system loads a treatment plan (e.g., which may have been generated according to method 500). The patient is then placed on a treatment couch, and x-ray images are taken of the patient. The treatment couch has six degrees of freedom of position, and so can be rotated about three axes and moved along three axes.

At block 605, a reference structure (e.g., the spine) is aligned to a treatment center of the treatment delivery system. The treatment delivery system may receive user inputs that adjust the couch position to align the patient's spine (or other reference structure) to the treatment center. The alignment is performed by aligning (registering) DRRs generated from the CT images with current x-ray images. Alignment is performed along six degrees of freedom (three translations and three rotations) using stereoscopic imaging data. The couch may be repositioned multiple times, and a new pair of x-ray images may be taken after each repositioning. The alignment is complete when the treatment delivery system determines that the alignment has only small residual corrections. In one embodiment, alignment is complete when the alignment is correct to within +/−10 mm in translations along each axis, +/−1 to +/−1.5 degrees in pitch, +/−1 to +/−1.5 degrees in roll and +/−1 to +/−3 degrees in yaw.

At block 610, the centroid of the ITV or of the partial-ITV is aligned to the treatment center of the treatment delivery system. In one embodiment, the couch is moved based on offset information included in the treatment plan so that the ITV's centroid (or partial-ITV's centroid) is positioned at the treatment center. Once the alignment is complete, the tumor's motion range should be centered at the treatment center. Note that alignment for a moving tumor involves understanding the motion range of the target tumor, and positioning the patient so that the center of that range of motion is aligned to the treatment center. In one embodiment, the system assists users in performing this alignment by enabling the user to acquire x-ray images at motion extremes (e.g., inhale and exhale points).

The method then continues to block 615 provided that an x-ray has been acquired since a last couch position change was performed. In one embodiment, external markers (e.g., light emitting diodes (LEDs)) should be attached to the patient before the method continues to block 615. In one embodiment, the method will not continue to block 615 until at least one external marker has been continuously visible for 3 or more consecutive respiratory cycles. The external markers are used to track the patient's respiratory cycle, and/or chest positions. A respiration model may be generated that correlates positions of the external markers to phases of the patient's respiratory cycle, and ultimately to tumor location and/or shape. The respiration model describes a non-rigid motion and deformation of the anatomical region as it undergoes its periodic motion (e.g. due to respiration), as a function of the instant in the respiration cycle, or as a function of external marker motion. The respiration model relates the locations of the targets to the locations of the external markers, as a function of the relative position in time within the respiration cycle. The respiration model may be constructed from the CT images and from motion cycle information obtained from sensors that track the external markers. The respiration model may be created during generation of the treatment plan and/or during treatment.

At block 615, the treatment delivery system begins treatment. This may include moving a linear accelerator (LINAC) to a first position and delivering radiation from that first position. During treatment, the target position is tracked in a single imaging plane or a single axis, depending on a tracking method being used (block 620). At block 625, a position of the LINAC and/or a position of the treatment couch may occasionally be adjusted during the treatment to compensate for motion that occurs in the imaging plane or axis. The adjustments are made based on the tracked target position. This ensures that a treatment beam delivers radiation to the partial-ITV, and thus to the target.

In one embodiment, a cross-check is performed using the imaging plane that is not being used to track the tumor. To perform the cross-check, the partial-ITV is first projected onto the x-axis. This defines the allowable target motion range in the x-axis. The position of the tumor in the imaging plane being used for tracking is then also projected onto the x-axis. The position of the tumor in the x-axis is then compared to the projection of the partial-ITV in the x-axis. If the tumor is within the range of the partial-ITV in the x-axis, then the cross-check indicates that the tumor position is valid. If the tumor is outside of the range of the partial-ITV in the x-axis, then the cross-check indicates that the tumor position is invalid. This may cause treatment to pause.

Figure 7:
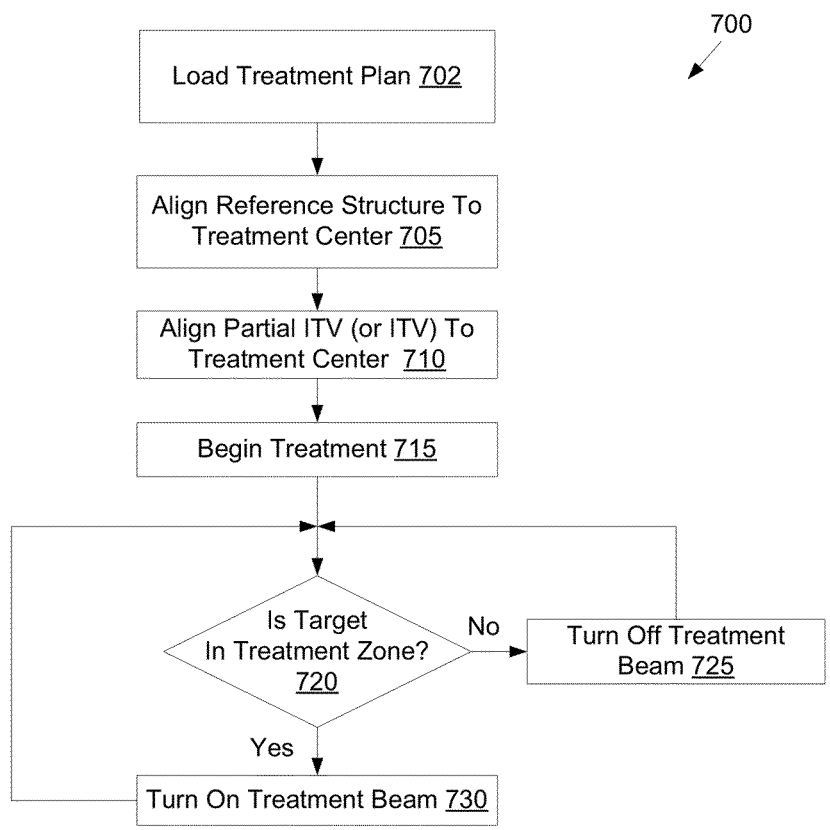
FIG. 7 illustrates a method of performing radiation treatment by a treatment delivery system that performs gated treatment delivery, in accordance with one embodiment of the present invention.

FIG. 7 illustrates a method 700 of performing radiation treatment by a treatment delivery system that performs gated treatment delivery, in accordance with one embodiment of the present invention. At block 702 of method 700, the treatment delivery system loads a treatment plan (e.g., which may have been generated according to method 500). The patient is then placed on a treatment couch, and x-ray images are taken of the patient.

At block 705, a reference structure (e.g., the spine) is aligned to a treatment center of the treatment delivery system. At block 710, the centroid of the ITV or partial-ITV is aligned to the treatment center of the treatment delivery system. At block 715, the treatment delivery system begins treatment. This may include moving a linear accelerator (LINAC) to a first position and delivering radiation from that first position. At block 720, the treatment delivery system determines whether the target is within a treatment zone. The treatment zone may be defined by a partial-ITV included in the treatment plan. The treatment delivery system may determine whether the target is within the treatment zone by tracking a position of the target. Alternatively, the treatment delivery system may monitor one or more reference structures and/or external markers to make such a determination (e.g., based on a respiration model). If the target is within the treatment zone, the method proceeds to block 730, and a treatment beam is activated (or is made to remain active). If the target is not within the treatment zone, the method continues to block 725, and the treatment beam is deactivated (or is made to remain off). This process continues until a prescribed dose of radiation has been delivered to the partial-ITV (and thus to the target tumor).

Figure 8:
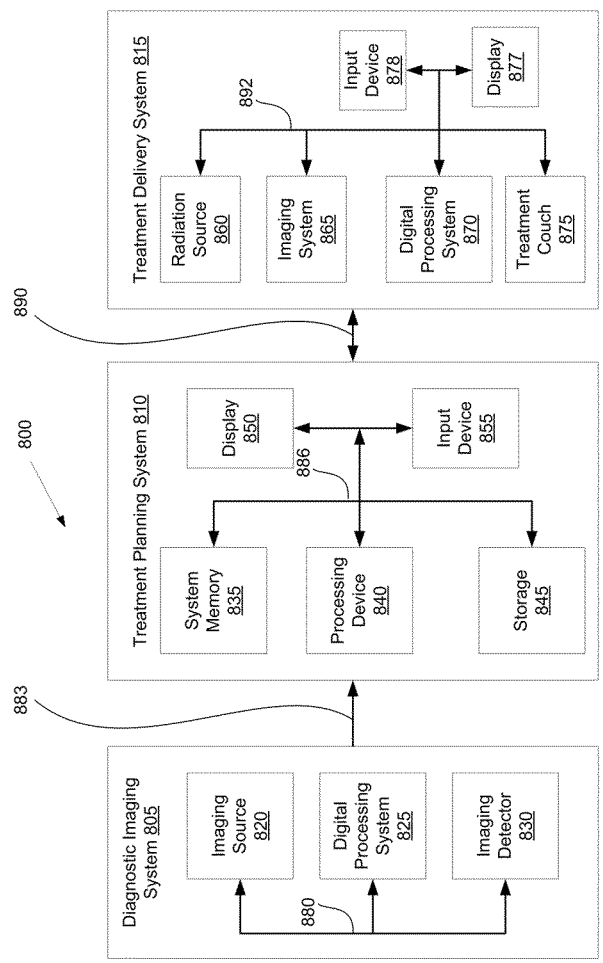
FIG. 8 illustrates one embodiment of systems that may be used in generating a simulation plan, performing simulation, and/or performing radiation treatment.

FIG. 8 illustrates one embodiment of systems that may be used in generating a simulation plan, performing simulation, and/or performing radiation treatment. These systems may be used to perform, for example, the methods described above. As described below and illustrated in FIG. 8, a system 800 may include a diagnostic imaging system 805, a treatment planning system 810, a treatment delivery system 815 and a motion detecting system (not shown). In one embodiment, the diagnostic imaging system 805 and the motion detecting system are combined into a single unit.

Diagnostic imaging system 805 may be any system capable of producing medical diagnostic images of a patient that may be used for subsequent medical diagnosis, treatment planning, treatment simulation and/or treatment delivery. For example, diagnostic imaging system 805 may be a computed tomography (CT) system, a magnetic resonance imaging (MRI) system, a positron emission tomography (PET) system, or the like. For ease of discussion, diagnostic imaging system 805 may be discussed below at times in relation to an x-ray imaging modality. However, other imaging modalities such as those above may also be used.

In one embodiment, diagnostic imaging system 805 includes an imaging source 820 to generate an imaging beam (e.g., x-rays) and an imaging detector 830 to detect and receive the beam generated by imaging source 820, or a secondary beam or emission stimulated by the beam from the imaging source (e.g., in an MRI or PET scan).

The imaging source 820 and the imaging detector 830 may be coupled to a digital processing system 825 to control the imaging operation and process image data. In one embodiment, diagnostic imaging system 805. In another embodiment, diagnostic imaging system 805 may receive imaging commands from treatment delivery system 815.

Diagnostic imaging system 805 includes a bus or other means 880 for transferring data and commands among digital processing system 825, imaging source 820 and imaging detector 830. Digital processing system 825 may include one or more general-purpose processors (e.g., a microprocessor), special purpose processor such as a digital signal processor (DSP) or other type of device such as a controller or field programmable gate array (FPGA). Digital processing system 825 may also include other components (not shown) such as memory, storage devices, network adapters and the like. Digital processing system 825 may be configured to generate digital diagnostic images in a standard format, such as the DICOM (Digital Imaging and Communications in Medicine) format, for example. In other embodiments, digital processing system 825 may generate other standard or non-standard digital image formats. Digital processing system 825 may transmit diagnostic image files (e.g., the aforementioned DICOM formatted files) to treatment delivery system 815 over a data link 883, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treat a patient despite the existence of a physical separation between the system user and the patient.

Treatment delivery system 815 includes a therapeutic and/or surgical radiation source 860 to administer a prescribed radiation dose to a target volume in conformance with a treatment plan. Treatment delivery system 815 may also include a digital processing system 870 to control radiation source 860, receive and process data from diagnostic imaging system 805 and/or motion detecting system 806, and control a patient support device such as a treatment couch 875. Digital processing system 870 may be configured to register 2D radiographic images received from diagnostic imaging system 805, from two or more stereoscopic projections, with digitally reconstructed radiographs (DRRs) generated by digital processing system 825 in diagnostic imaging system 805 and/or DRRs generated by processing device 840 in treatment planning system 810. Digital processing system 870 may include one or more general-purpose processors (e.g., a microprocessor), special purpose processor such as a digital signal processor (DSP) or other type of device such as a controller or field programmable gate array (FPGA). Digital processing system 870 may also include other components (not shown) such as memory, storage devices, network adapters and the like.

In one embodiment, digital processing system 870 includes system memory that may include a random access memory (RAM), or other dynamic storage devices, coupled to a processing device, for storing information and instructions to be executed by the processing device. The system memory also may be used for storing temporary variables or other intermediate information during execution of instructions by the processing device. The system memory may also include a read only memory (ROM) and/or other static storage device for storing static information and instructions for the processing device.

Digital processing system 870 may also include a storage device, representing one or more storage devices (e.g., a magnetic disk drive or optical disk drive) for storing information and instructions. The storage device may be used for storing instructions for performing the treatment delivery steps discussed herein. Digital processing system 870 may be coupled to radiation source 860 and treatment couch 875 by a bus 892 or other type of control and communication interface.

Digital processing system 870 may implement methods to manage timing of diagnostic x-ray imaging in order to maintain alignment of a target with a radiation treatment beam delivered by the radiation source 860.

Treatment delivery system 815 may include imaging system 865 to image a target. In one embodiment, the treatment delivery system 815 includes an input device 878 and a display 877 connected with digital processing system 870 via bus 892. The display 877 can show trend data that identifies a rate of target movement (e.g., a rate of movement of a target volume that is under treatment). The display can also show a current radiation exposure of a patient and a projected radiation exposure for the patient. The input device 878 can enable a clinician to adjust parameters of a treatment delivery plan during treatment.

Treatment planning system 810 includes a processing device 840 to generate and modify treatment plans and/or simulation plans. Processing device 840 may represent one or more general-purpose processors (e.g., a microprocessor), special purpose processor such as a digital signal processor (DSP) or other type of device such as a controller or field programmable gate array (FPGA). Processing device 840 may be configured to execute instructions for performing simulation generating operations and/or treatment planning operations discussed herein.

Treatment planning system 810 may also include system memory 835 that may include a random access memory (RAM), or other dynamic storage devices, coupled to processing device 840 by bus 886, for storing information and instructions to be executed by processing device 840. System memory 835 also may be used for storing temporary variables or other intermediate information during execution of instructions by processing device 840. System memory 835 may also include a read only memory (ROM) and/or other static storage device coupled to bus 886 for storing static information and instructions for processing device 840.

Treatment planning system 810 may also include storage device 845, representing one or more storage devices (e.g., a magnetic disk drive or optical disk drive) coupled to bus 886 for storing information and instructions. Storage device 845 may be used for storing instructions for performing the treatment planning steps discussed herein.

Processing device 840 may also be coupled to a display device 850, such as a cathode ray tube (CRT) or liquid crystal display (LCD), for displaying information (e.g., a 2D or 3D representation of the VOI) to the user. An input device 855, such as a keyboard, may be coupled to processing device 840 for communicating information and/or command selections to processing device 840. One or more other user input devices (e.g., a mouse, a trackball or cursor direction keys) may also be used to communicate directional information, to select commands for processing device 840 and to control cursor movements on display 850.

Treatment planning system 810 may share its database (e.g., data stored in storage 845) with a treatment delivery system, such as treatment delivery system 815, so that it may not be necessary to export from the treatment planning system prior to treatment delivery. Treatment planning system 810 may be linked to treatment delivery system 815 via a data link 890, which may be a direct link, a LAN link or a WAN link.

It should be noted that when data links 883 and 890 are implemented as LAN or WAN connections, any of diagnostic imaging system 805, treatment planning system 810 and/or treatment delivery system 815 may be in decentralized locations such that the systems may be physically remote from each other. Alternatively, any of diagnostic imaging system 805, treatment planning system 810, and/or treatment delivery system 815 may be integrated with each other in one or more systems.

Figure 9:
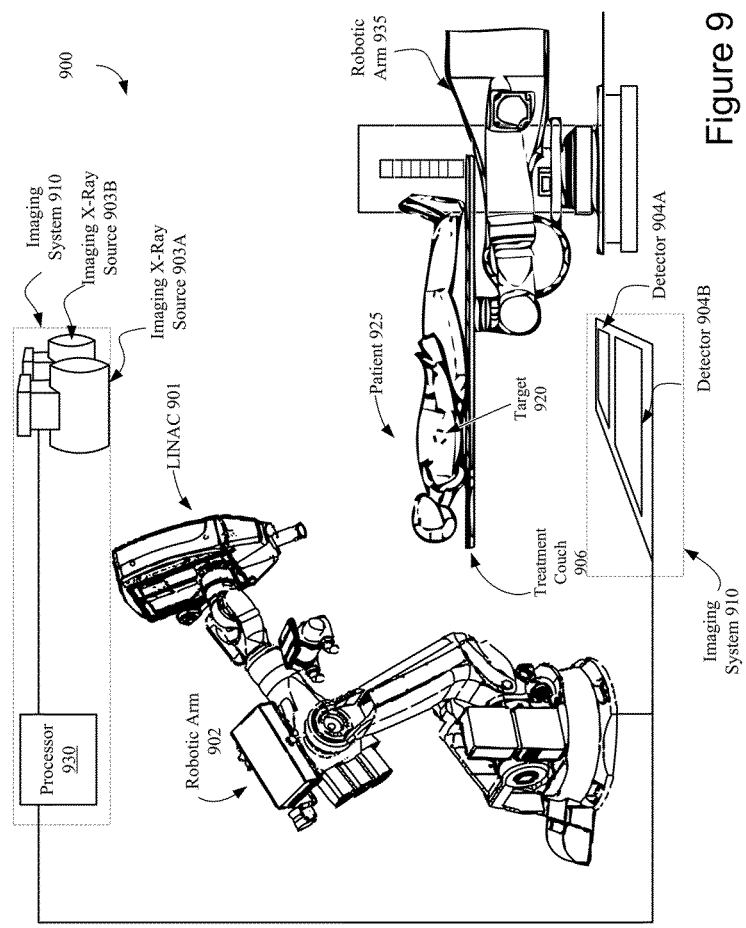
FIGS. 9 and 10 illustrate configurations of image-guided radiation treatment systems, in accordance with embodiments of the present invention.
Figure 10:
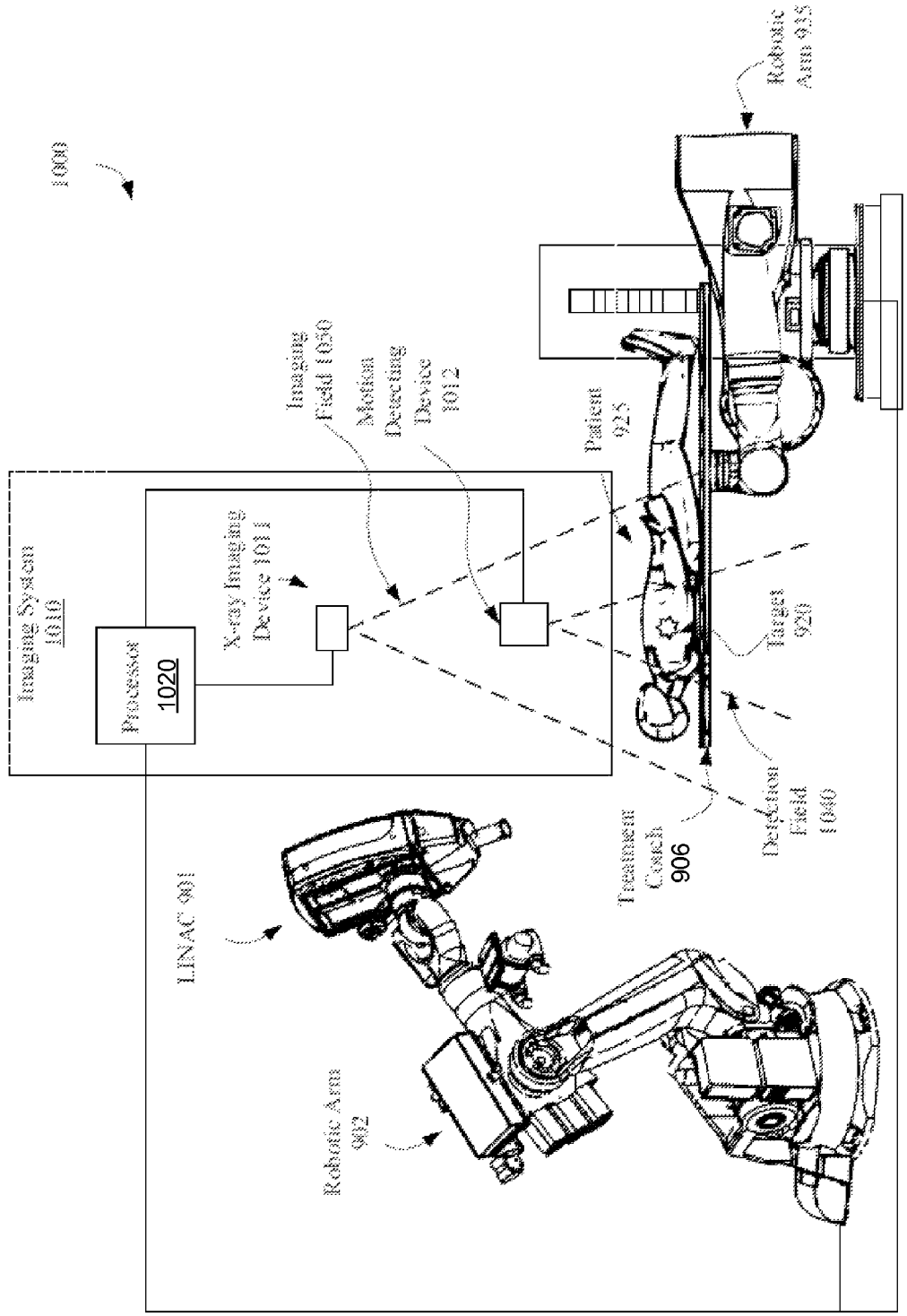

FIGS. 9 and 10 illustrate configurations of image-guided radiation treatment systems 900 and 1000, in accordance with embodiments of the present invention. In the illustrated embodiments, the radiation treatment systems 900 and 1000 include a linear accelerator (LINAC) 901 that acts as a radiation treatment source. The LINAC 901 is mounted on the end of a robotic arm 902 having multiple (e.g., 5 or more) degrees of freedom in order to position the LINAC 901 to irradiate a pathological anatomy (e.g., target 920) with beams delivered from many angles, in many planes, in an operating volume around a patient. Treatment may involve beam paths with a single isocenter, multiple isocenters, or with a non-isocentric approach. Alternatively, other types of image guided radiation treatment (IGRT) systems may be used. In one alternative embodiment, the LINAC 1001 may be mounted on a gantry based system to provide isocentric beam paths. In one particular embodiment, the IGRT system is the Vero SBRT System (referred to as TM200 in Japan), a joint product of Mitsubishi Heavy Industries Ltd., of Tokyo Japan and BrainLAB AG of Germany, that utilizes a rigid O-ring based gantry. Such an O-ring based gantry system is described in greater detail below with reference to FIG. 11. In another embodiment, a C-arm based gantry system is used, such as the gantry system of Varian®.

The LINAC 901 may be positioned at multiple different nodes (predefined positions at which the robot stops and radiation may be delivered) during treatment by moving the robotic arm 902. At the nodes, the LINAC 901 can deliver one or more radiation treatment beams to a target. The nodes may be arranged in an approximately spherical distribution about a patient. The particular number of nodes and the number of treatment beams applied at each node may vary as a function of the location and type of pathological anatomy to be treated. For example, the number of nodes may vary from 50 to 300, or more preferably 15 to 100 nodes and the number of beams may vary from 1100 to 3200, or more preferably 50 to 300.

Referring to FIG. 9, radiation treatment system 900, in accordance with one embodiment of the present invention, includes an imaging system 910 having a processor 930 connected with x-ray sources 903A and 903B and fixed x-ray detectors 904A and 904B. Alternatively, the x-ray sources 903A, 903B and/or x-ray detectors 904A, 904B may be mobile, in which case they may be repositioned to maintain alignment with the target 920, or alternatively to image the target from different orientations or to acquire many x-ray images and reconstruct a three-dimensional (3D) cone-beam CT. In one embodiment the x-ray sources are not point sources, but rather x-ray source arrays, as would be appreciated by the skilled artisan. In one embodiment, LINAC 901 serves as an imaging source (whether gantry or robot mounted), where the LINAC power level is reduced to acceptable levels for imaging.

Imaging system 910 may perform computed tomography (CT) such as cone beam CT, and images generated by imaging system 901 may be two-dimensional (2D) or three-dimensional (3D). The two x-ray sources 903A and 903B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 906 during treatment) and to illuminate imaging planes of respective detectors 904A and 904B after passing through the patient. In one embodiment a robotic arm 935 is used for positioning the patient. Imaging system 910, thus, provides stereoscopic imaging of the target 920 and the surrounding volume of interest (VOI). In other embodiments, imaging system 910 may include more or less than two x-ray sources and more or less than two detectors, and any of the detectors may be movable rather than fixed. In yet other embodiments, the positions of the x-ray sources and the detectors may be interchanged. Detectors 904A and 904B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

Referring to FIG. 10, in alternative embodiments an imaging system 1010 includes a processor 1020 connected to a motion detection device 1012 to determine target motion, the motion detecting device 1012 having a detection field 1040. The motion detecting device 1012 may detect external patient motion (such as chest movement during respiration) that occurs within an imaging field 1050 of an x-ray imaging device 1011, which may also be connected to the processor 1020. The motion detecting device 1012 can be any sensor or other device capable of identifying target movement. The motion detecting device 1012, may be, for example an optical sensor such as a camera, a pressure sensor, an electromagnetic sensor, or some other sensor that can provide motion detection without delivering ionizing radiation to a user (e.g., a sensor other than an x-ray imaging system). In one embodiment, the motion detecting device 1012 acquires measurement data indicative of target motion in real-time. Alternatively, the measurement data may be acquired at a frequency that is higher (potentially substantially higher) than can be achieved or than is desirable with x-ray imaging (due to ionizing radiation delivered to the patient with each x-ray image). In one embodiment, the motion detecting device 1012 does not provide a high absolute position accuracy.

Instead, the motion detecting device 1012 may provide sufficient relative position accuracy to detect patient movement and/or target movement.

In one embodiment, the motion detecting device 1012 is an optical system, such as a camera. The optical system may track the position of light-emitting diodes (LEDs) situated on patient 925. Alternatively, the optical system may directly track a surface region of patient 925, as distinguished from tracking LEDs on the patient. There may be a correlation between movement of the target and movement of the LEDs and/or surface region of the patient 925. Based on the correlation, when motion of the LEDs and/or surface region is detected, it can be determined that the target 920 has also moved sufficiently to require another diagnostic x-ray image to precisely determine the location of the target.

Figure 11:
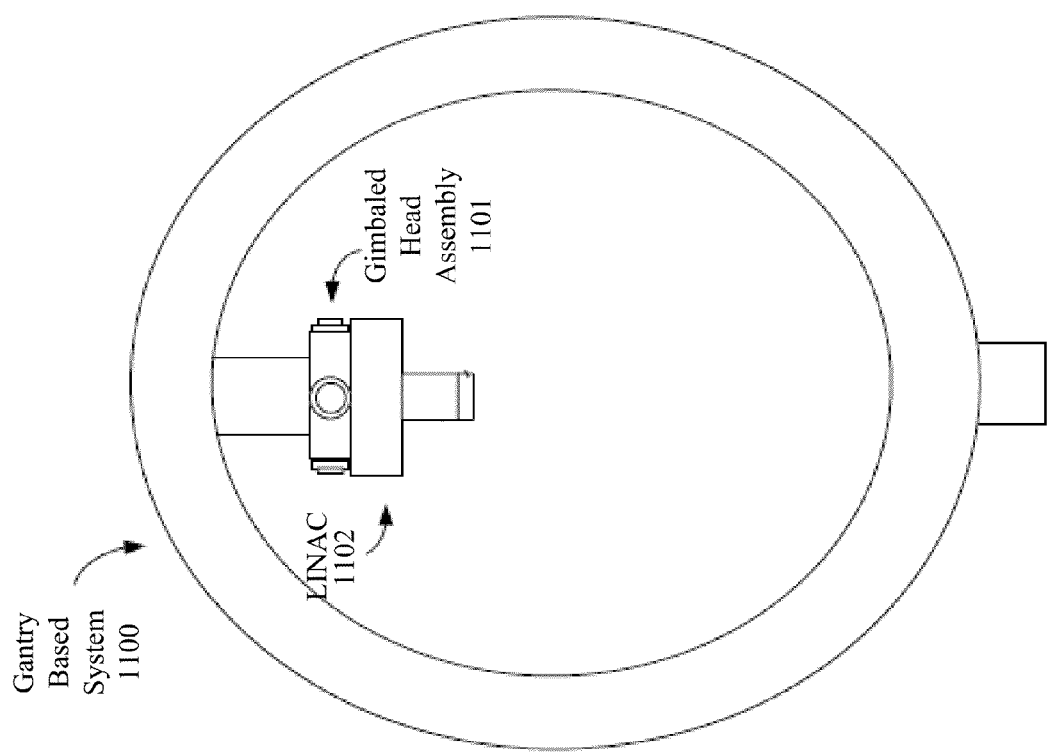
FIG. 11 illustrates one embodiment of a gantry based (isocentric) intensity modulated radiotherapy (IMRT) system.

FIG. 11 illustrates one embodiment of a gantry based (isocentric) intensity modulated radiotherapy (IMRT) system 1100. In a gantry based system 1100, a radiation source (e.g., a LINAC) 1102 is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator (MLC) that allows portions of the beam to be blocked, so that the remaining beam incident on the patient has a pre-defined shape. Additionally, in IMRT, the shape of each radiation beam can be changed while the beam is being delivered, to allow the dose to be maximally conformal to the target and spare critical structures as much as possible. The resulting system generates arbitrarily shaped radiation beams that intersect each other at the isocenter to deliver a dose distribution to the target.

In one embodiment, the gantry based system 1100 is an o-ring based system having a gimbaled radiation source head assembly 1101. The o-ring can be skewed around its vertical axis, and the gimbals can be driven to rotate in pan and tilt directions in order to position the linear accelerator 1102. In one embodiment, the gantry rotates 360 degrees about a horizontal axis, and additionally allows rotation about a vertical axis (a so called skew) of +/−60 degrees. Orthogonal gimbals hold the LINAC 1102, which allows pan and tilt motions of the LINAC. This system may include dual orthogonal imaging systems at 45 degrees from the treatment beam, to allow for the acquisition of x-ray images.

In one embodiment, the gantry based system 1100 includes an EPID (not shown). The EPID uses a treatment beam to generate a 1D or 2D image of a target region.

It will be apparent from the foregoing description that aspects of the present invention may be embodied, at least in part, in software. That is, the techniques may be carried out in a computer system or other data processing system in response to its processor, such as digital processing system 870, for example, executing sequences of instructions contained in a memory. In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as digital processing system 870.

A machine-readable medium can be used to store software and data which when executed by a general purpose or special purpose data processing system causes the system to perform various methods of the present invention. This executable software and data may be stored in various places including, for example, system memory and storage or any other device that is capable of storing software programs and/or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc.

Unless stated otherwise as apparent from the foregoing discussion, it will be appreciated that terms such as "processing," "computing," "generating," "treating" "determining," "setting," "adjusting" or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, implemented by a computing system programmed to perform the following, comprising:

determining a full motion range of a target, wherein the full motion range of the target defines an internal target volume (ITV);

identifying a partial motion range of the target, wherein the partial motion range is an untracked portion of the full motion range of the target comprising one of an untracked plane or an untracked axis; and generating a partial-ITV based on the identified partial motion range, wherein the partial-ITV is a volume swept by the target as the target moves through the partial motion range, the partial-ITV being smaller than the ITV.

2. The method of claim 1, wherein determining the full motion range of the target comprises:
   acquiring two preoperative images of the target that show two different positions of the full motion range;
   receiving delineations of the target in the two preoperative images; and
   interpolating the full motion range of the target based on the delineations of the target in the two preoperative images.

3. The method of claim 1, further comprising:
   generating a treatment plan to deliver treatment to the partial-ITV.

4. The method of claim 3, wherein identifying the partial motion range comprises at least one of receiving a user selection of the partial motion range or automatically computing the partial motion range based on at least one of a tracking mode or a treatment mode identified in the treatment plan.

5. The method of claim 1, wherein the target travels through the full motion range during a respiration cycle of a patient, the method further comprising:
   monitoring the respiration cycle of the patient based on external markers; and
   generating a respiration model that correlates positions of the external markers to phases of the respiration cycle and to a target position.

6. The method of claim 5, further comprising:
   when the patient is in one or more particular phases of the respiration cycle, activating a radiation treatment beam to treat the partial-ITV, wherein the partial-ITV includes all possible target positions during the one or more particular phases of the respiration cycle; and
   when the patient is in other phases of the respiration cycle, deactivating the radiation treatment beam.

7. The method of claim 1, the method further comprising:
   determining when the target is located at positions that are within the partial-ITV;
   while the target is located at the positions within the partial-ITV, activating a radiation treatment beam to treat the volume swept by the target as the target moves through the partial motion range; and
   deactivating the treatment beam while the target is outside of the partial-ITV.

8. The method of claim 1, wherein a tracking mode that tracks the target along a single axis will be used during treatment, the method further comprising:
   identifying the partial motion range by projecting the full motion range of the target onto a plane that is normal to the tracked axis, wherein the partial-ITV covers a motion range of the target the untracked plane.

9. The method of claim 1, wherein a tracking mode that tracks the target along a single imaging plane will be used during treatment, the method further comprising:
   identifying the partial motion range by projecting the full motion range of the target onto an axis that is normal to the single imaging plane, wherein the partial-ITV covers a motion range of the target in the untracked axis.

10. The method of claim 1, further comprising:
    aligning a reference structure to a treatment center of a treatment system in three dimensions (3D) by acquiring images by a first image detector and a second image detector and registering the images to a preoperative 3D image;
    aligning a center of the partial-ITV to the treatment center based on a known offset between the reference structure and the center of the partial-ITV;
    tracking target position in an imaging plane that is parallel to a treatment plane that intersects the treatment center using one of the first image detector or the second image detector; and
    converting image data from the first image detector or the second image detector into 3D positional data by projecting a 2D target position identified in the image data onto the treatment plane.

11. The method of claim 1, further comprising:
    aligning the target to a treatment center of a treatment system in three dimensions (3D) by acquiring a 3D image of the patient and performing a registration between said 3D image and a previous 3D image of the patient; and
    tracking target position in an imaging plane using a first image detector.

12. A treatment planning system, comprising:
    a memory to store instructions for image guided treatment planning; and
    a processing device coupled to memory, the processing device configured to:
       determine a full motion range of a target, wherein the full motion range of the target defines an internal target volume (ITV);
       identify a partial motion range of the target, wherein the partial motion range is an untracked portion of the full motion range of the target comprising one of an untracked plane or an untracked axis;
       generate a partial-ITV based on the identified partial motion range, wherein the partial-ITV is a volume swept by the target as the target moves through the partial motion range, the partial-ITV being smaller than the ITV; and
       generate a treatment plan that includes instructions for delivering treatment to the partial-ITV.

13. The system of claim 12, wherein the processing device is further configured to:
    receive delineations of the target in two preoperative images that show two different positions of the motion range; and
    interpolate the full motion range of the target based on the delineations of the target in the two preoperative images.

14. The system of claim 12, wherein identifying the partial motion range comprises at least one of receiving a user selection of the partial motion range or automatically computing the partial motion range based on at least one of a tracking mode or a treatment mode identified in the treatment plan.

15. The system of claim 12, further comprising:
    a motion tracking system to monitor a respiration cycle of a patient based on external markers, wherein the target travels through the full motion range during the respiration cycle of the patient;
    wherein the processing device is further configured to generate a respiration model that correlates positions of the external markers to phases of the respiration cycle and to a target position; and
    wherein the treatment plan is for gated radiation treatment in which a radiation treatment beam is activated while the target is located within the partial-ITV and is deactivated while the target is located outside of the partial-ITV.

16. The system of claim 1, wherein the tracking mode tracks the target along a single axis, and wherein the processing device is further configured to identify the partial motion range by projecting the full motion range of the target onto a plane that is normal to the tracked axis, wherein the partial-ITV covers a motion range of the target in the untracked plane.

17. The system of claim 1, wherein the tracking mode tracks the target along a single imaging plane, and wherein the processing device is further configured to identify the partial motion range by projecting the full motion range of the target onto an axis that is normal to the single imaging plane, wherein the partial-ITV covers a motion range of the target in the untracked axis.

18. A treatment delivery system comprising:
a treatment bed to support a patient during a treatment;
at least one imager to generate images of the patient that include a target during treatment;
a radiation source to generate a radiation treatment beam; and
a processor to perform the following, comprising:
load a treatment plan, wherein the treatment plan identifies a partial internal target volume (partial-ITV), the partial-ITV including a volume swept by the target as the target moves through a partial motion range, wherein the partial motion range is a subset of a full motion range of the target that defines an internal target volume (ITV);
align a center of the partial-ITV to a treatment center of the treatment delivery system based on positioning the treatment bed;
monitor a current target position based on images generated by the at least one imager; and
activate the radiation source to deliver the radiation treatment beam to the partial-ITV while minimizing radiation delivered to areas outside of the partial-ITV.

19. The treatment delivery system of claim 18, wherein the at least one imager comprises an x-ray imager that has an imaging plane, and wherein the partial motion range corresponds to motion along an untracked axis that is normal to the imaging plane, further comprising the processor to:
track the current target position within the imaging plane in two dimensions (2D) based on x-ray images generated by the x-ray imager;
convert a 2D target position determined from the x-ray images into three dimensional (3D) positional data by projecting the 2D target position onto a treatment plane, wherein the treatment plane is a plane that passes through the treatment center and that is plane parallel to the imaging plane; and
reposition the radiation source to deliver the radiation treatment beam to the target based on the current target position.

20. The treatment delivery system of claim 18, wherein the treatment delivery system is a gantry based system configured to perform gated treatment delivery, and wherein the processor is configured to activate the radiation source when the target is located within the partial-ITV and to deactivate the radiation source when the target is located outside of the partial-ITV.

21. The treatment delivery system of claim 20, further comprising:
a motion detecting device to track positions of one or more external markers disposed on the patient;
wherein the processing device is further configured to determine when the target is located within the partial-ITV and when the target is located outside of the partial-ITV based on correlating the positions of the one or more external markers to locations of the target using a respiratory model.

22. The treatment delivery system of claim 18, wherein the at least one imager includes an electronic portal imaging device (EPID), and wherein the processor is further configured to perform the following, comprising:
track the current target position within an imaging axis in one dimension (1D) based on the images, which are generated by the EPID; and
reposition the radiation source to deliver the radiation treatment beam to the target based on the current target position, wherein the processor accounts for target motion outside of the imaging axis by treating the partial-ITV, the partial-ITV including the volume swept by the target in a plane to which the imaging axis is normal.

* * * * *